United States Patent
Story

(10) Patent No.: US 6,193,516 B1
(45) Date of Patent: Feb. 27, 2001

(54) DENTAL IMPLANT HAVING A FORCE DISTRIBUTION SHELL TO REDUCE STRESS SHIELDING

(75) Inventor: Brooks J. Story, Carlsbad, CA (US)

(73) Assignee: Sulzer Calcitek Inc., Carlsbad, CA (US)

( * ) Notice: Subject to any disclaimer, the term of this patent is extended or adjusted under 35 U.S.C. 154(b) by 0 days.

(21) Appl. No.: 09/336,322

(22) Filed: Jun. 18, 1999

(51) Int. Cl.[7] .................................................. A61C 8/00

(52) U.S. Cl. ........................................ 433/173; 433/201.1

(58) Field of Search ..................................... 433/172, 173, 433/174, 175, 176, 201.1

(56) References Cited

U.S. PATENT DOCUMENTS

| | | | |
|---|---|---|---|
| 4,178,686 | * 12/1979 | Riess et al. | 433/173 |
| 4,270,905 | * 6/1981 | Mohammed | 433/201.1 |
| 4,978,358 | 12/1990 | Bobyn | 623/23 |
| 5,181,930 | 1/1993 | Dumbleton et al. | 623/23 |
| 5,314,492 | 5/1994 | Hamilton et al. | 623/23 |
| 5,316,476 | * 5/1994 | Krauser | 433/173 |
| 5,370,696 | 12/1994 | Jamison et al. | 623/16 |
| 5,397,365 | 3/1995 | Trentacosta | 623/18 |
| 5,449,291 | * 9/1995 | Lueschen et al. | 433/173 |
| 5,468,150 | * 11/1995 | Brammann | 433/173 |
| 5,478,237 | * 12/1995 | Ishizawa | 433/173 |
| 5,480,449 | 1/1996 | Hamilton et al. | 623/66 |
| 5,881,443 | * 3/1999 | Roberts et al. | 29/446 |

FOREIGN PATENT DOCUMENTS

WO 91/18563   12/1991   (WO).

OTHER PUBLICATIONS

Reilly, D.T., et al., "Carbon Fiber Reinforced Polyetherketone Composite Femoral Stems in Dogs: Two–Year Remolding", The 20th Annual Meeting of the Society for Biomaterials,Apr. 5–9, 1994, p. 50.

Lumbardo, D.F., et al., "Measured Periprosthetic Bone Changes Following Six Year Canine Implantation with a Composite Hip Prosthesis",, The 20th Annual Meeting of the Society for Biomaterials,Apr. 5–9, 1994, p. 51.

Marcolongo, M., et al., "The Effect of Hip Implant Stiffness and Fixation on Bone Strains Using an Experimentally Validated Model",, The 20th Annual Meeting of the Society for Biomaterials, Apr. 5–9, 1994, p. 56.

Overland, M.K., et al., "Residual Stresses in Two Orthopedic Composite Materials",, The 20th Annual Meeting of the Society for Biomaterials,Apr. 5–9, 1994, p. 159.

D'Ariano, M.D., et al., "Long Term Shear Strength Durability of CF/PEEK Composite in Physiologic Saline",, The 20th Annual Meeting of the Society for Biomaterials,Apr. 5–9, 1994, p. 184.

Overland, M. K., et al., "The Influence of Radiation sterilization on the Tensile Strength of Lipid Conditioned PSF and PEEK Polymers",, The 20th Annual Meeting of the Society for Biomaterials, Apr. 5–9, 1994, p. 191.

Mayer, J., et al., "Knitted Carbon Fiber Reinforced Biocompatible Structures:A New Biomaterial for Load Bearing Implants with Homoelsaticity to Bone",, The 20th Annual Meeting of the Society for Biomaterials,Apr. 5–9, 1994, p. 230.

(List continued on next page.)

Primary Examiner—John J. Wilson
(74) Attorney, Agent, or Firm—Philip S. Lyren

(57) ABSTRACT

A dental implant that reduces the potential for stress shielding. The dental implant utilizes an implant body that includes a metallic core and a shell disposed about the metallic core. The shell is made from a material that has a lower modulus of elasticity than the metallic core. The metallic core also is connected to a mounting end to which a prosthetic tooth may ultimately be attached.

20 Claims, 3 Drawing Sheets

OTHER PUBLICATIONS

Maharaj, G., et al.,"Characterization of Wear in Composite Material Orthopaedic Implants Part I: The Composite Trunnion/Ceramic Head Interface",Bio–Medical Materials and Engineering, vol. 4, No. 3, 1994, pp. 193–198.

Albert, K., et al., "Characterization of Wear in Composite Material Orthopaedic Implants, Part II: The Implant/Bone Interface",Bio–Medical Materials and Engineering, vol. 4, No. 3, 1994, pp. 199–211.

Yildiz, H., et al., "Composite Hip Prosthesis Design.I-.Analysis",Composite Hip Prosthesis.II., pp. 90–119.

Shono, Y., et al. "A Biomechanical Analysis of Decompression and Reconstruction Methods in the Cervical Spine", The Journal of Bone and Joint Surgery, vol. 75–A, No. 11, Nov. 1993, pp. 1674–1684.

Akay, M., et al., "Numerical and Experimental Stress Analysis of a Polymeric Composite Hip Joint Prosthesis",Journal of Biomedical Materials Research, vol. 31, 1996, pp. 167–182.

Szivek, J. A., et al., "Strain Redistribution in the Canine Femur Resulting from Hip Implants of Different Stiffness", Journal of Investigative Surgery, vol. 7, pp. 95–110.

Jones, D. W., et al., "Strength and Modulus of Elasticity of Composite Materials",23rd Annual Meeting of the Society for Biomaterials,Apr. 30–May 4, 1997, p. 311.

* cited by examiner

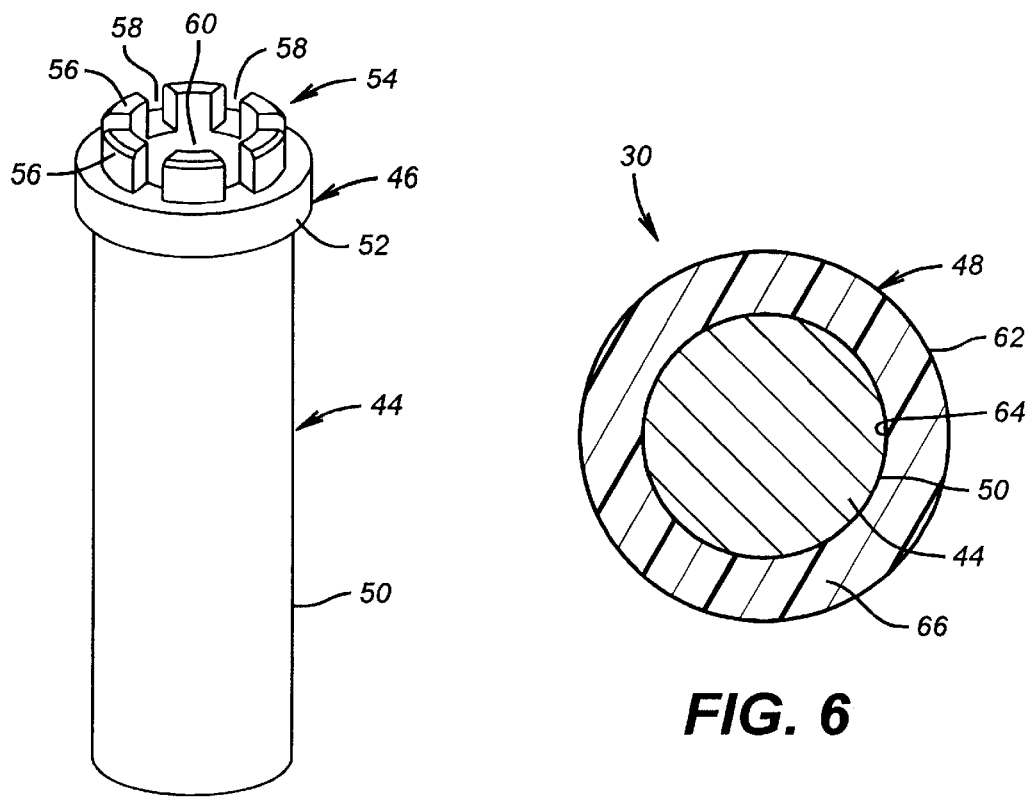
FIG. 6
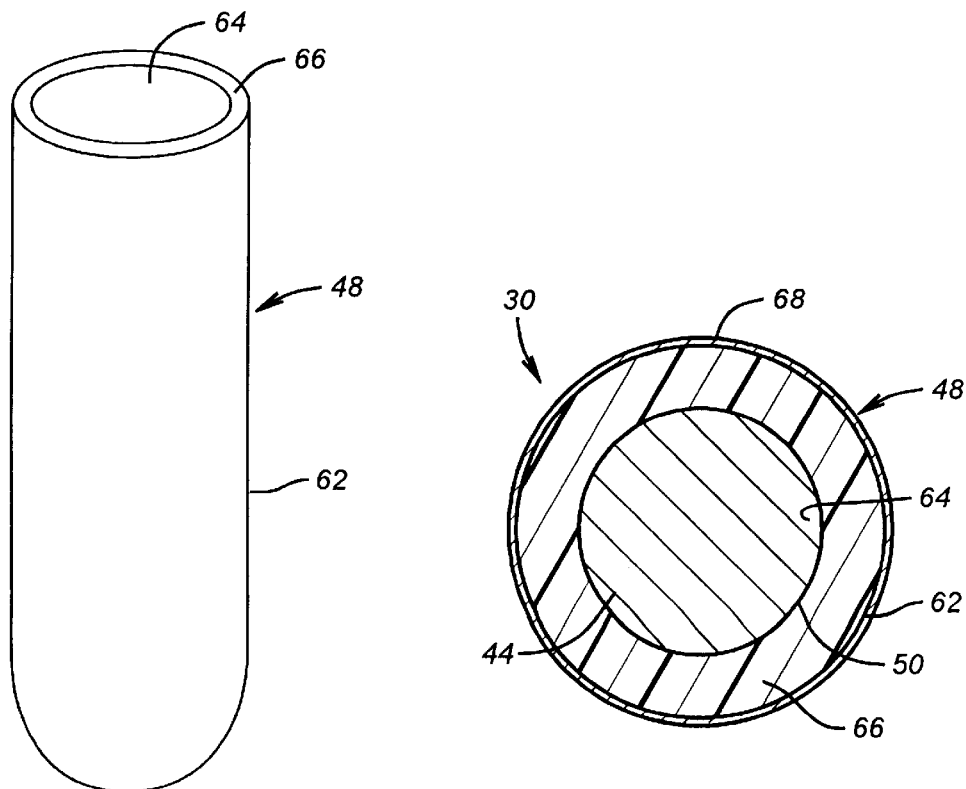
FIG. 7
FIG. 5

DENTAL IMPLANT HAVING A FORCE DISTRIBUTION SHELL TO REDUCE STRESS SHIELDING

FIELD OF THE INVENTION

The present invention relates generally to prosthetic implants, and particularly to dental implants that are designed to distribute forces, created during mastication, to surrounding bone. This distribution of forces reduces stress shielding of the surrounding bone.

BACKGROUND OF THE INVENTION

A variety of dental implants currently are known and available. The implants are designed for insertion into the maxilla or mandible, e.g. jawbone, of a patient to support the mounting of a prosthetic tooth. Generally, a cylindrical hole is formed in the mandible or jawbone of the patient, and the implant is mounted in the hole and allowed to undergo osseointegration.

A dental implant includes a generally cylindrical body designed for placement in the cylindrical hole formed in the jawbone of a patient. The generally cylindrical body may be threaded. The exposed or coronal end of the dental implant includes a mounting feature or features that aid in the mounting of a prosthetic tooth. For example, the coronal end may include a splined interface and a threaded bore to which an abutment and prosthetic tooth are ultimately mounted.

Conventionally, the body of the dental implant has been formed from titanium or a titanium alloy, such as Ti6Al4V. Such titanium materials have served well in enhancing bone attachment to the surface of the dental implant.It is believed that a stable oxide forms on the titanium or titanium alloy, and serves as a suitable surface for enhancing the desirable attachment between bone and the dental implant.

Despite their proven record in promoting osseointegration, titanium and titanium alloys present certain other challenges to providing an optimal dental implant. Titanium and suitable titanium alloys are orders of magnitude higher in stiffness than human bone, and therefore dental implants formed from such materials absorb most of the forces of mastication. This can lead to a phenomenon known as Astress shielding of the surrounding bone.

Specifically, it has been determined that inadequate stimulation of bone tissue over extended periods causes the bone tissue to be resorbed by the body, an effect commonly known as Wolff s Law. This effect becomes apparent when bone surrounding the dental implant is not adequately stimulated due to, for instance, absorption of a majority of forces created during mastication by a stiff dental implant. The lack of stimulation can cause saucerization, otherwise known as bone die-back, which progresses around the upper portion of an otherwise healthy dental implant. The loss of bone can lead to destabilization and even loosening of the dental implant. Additionally, once sufficient bone tissue has undergone resorption, portions of the implant body become exposed, and this surface, which is typically textured to provide high surface area, is susceptible to infection.

It would be advantageous to design a dental implant able to transmit the forces of mastication to surrounding bone tissue without being unduly subject to degradation or breakage.

SUMMARY OF THE INVENTION

The present invention features a dental implant comprising an implant body. The implant body includes a metallic core and an anti-rotational mounting feature connected to the metallic core. Additionally, a shell is disposed about the metallic core. The shell has a lower modulus of elasticity than the metallic core to facilitate transfer of force to surrounding bone tissue.

According to another aspect of the invention, a dental implant is designed for implantation at an implant site in a maxilla or mandible of a patient. The dental implant comprises a metallic core and a shell. The shell includes a recessed opening sized to receive at least a portion of the metallic core. The shell includes an outer surface sized to fit within a cylindrical hole formed in the mandible at the implant site. Additionally, the shell is formed of a less stiff material than the metallic core to facilitate transfer of forces from the dental implant to the surrounding bone tissue.

According to a further aspect of the invention, a dental implant is provided for implantation at an implant site which includes a cylindrical hole formed in a mandible or maxilla of a patient. The dental implant comprises a mounting end to which a prosthetic tooth can be attached. Additionally, a force dissipater is coupled to the mounting end. The force dissipater is sized for insertion into the hole formed in the mandible. This force dissipater effectively distributes a substantial portion of the forces, generated during mastication, to the mandible surrounding the force dissipater.

BRIEF DESCRIPTION OF THE DRAWINGS

The invention will hereafter be described with reference to the accompanying drawings, wherein like reference numerals denote like elements, and:

FIG. 5 is an exploded view of the dental implant illustrated in FIG. 4;

FIG. 6 is a cross-sectional view taken generally along line 6-6 of FIG. 4; and

FIG. 7 is a cross-sectional view similar to FIG. 6 but showing an alternate embodiment of the dental implant.

DETAILED DESCRIPTION OF THE PREFERRED EMBODIMENTS

Figure 1:
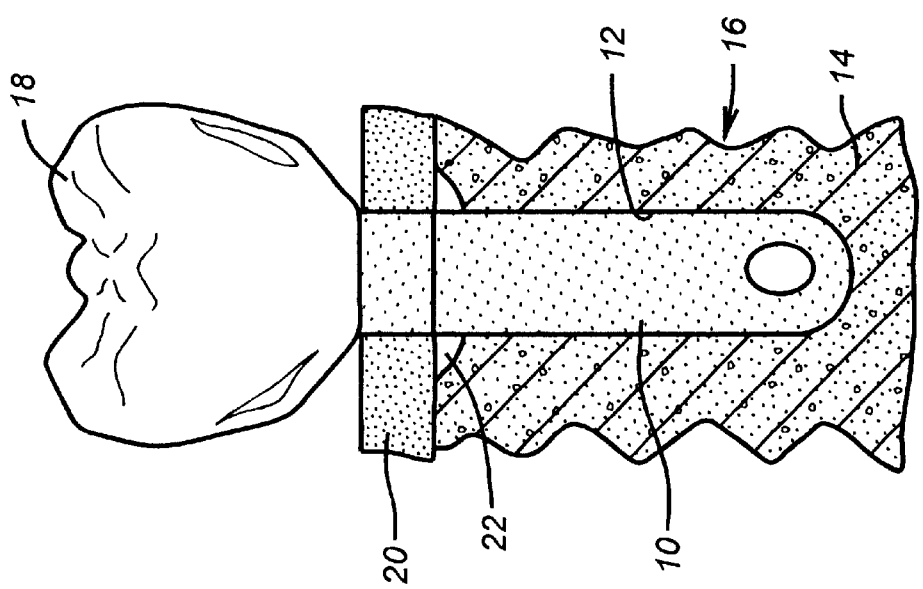
FIG. 1 is a front view of a conventional dental implant and prosthetic tooth mounted in a mandible of a patient.

The stiffness of conventional dental implants can lead to saucerization of the bone tissue surrounding the upper region of the dental implant, as illustrated in FIG. 1. In this illustration, a conventional titanium or titanium alloy dental implant 10 is shown implanted within a cylindrical bore 12. Cylindrical bore 12 is formed in an appropriate area of bone tissue 14 at an implant site 16.

A prosthetic tooth 18 is mounted to dental implant 10, and a naturally occurring layer of gingival tissue 20 is disposed between bone tissue 14 and prosthetic tooth 18. As chewing or mastication forces act on prosthetic tooth 18, those forces are translated through dental implant 10. However, because of the stiffness of the titanium or titanium alloy from which dental implant 10 is formed, most of the forces are absorbed by the implant, leading to a reduction in stress transfer to the bone tissue 14. If the bone tissue is inadequately stimulated for an extended period of time, the tissue begins to be resorbed by the body. This effect is most pronounced in the more dense cortical bone located near the surface of the jawbone, as opposed to the spongy, or trabecular, bone in the inner regions on the jawbone. This leads to an area of saucerization 22 in which bone tissue actually disappears around the portion of the dental implant proximate gingival tissue 20.

Figure 2:
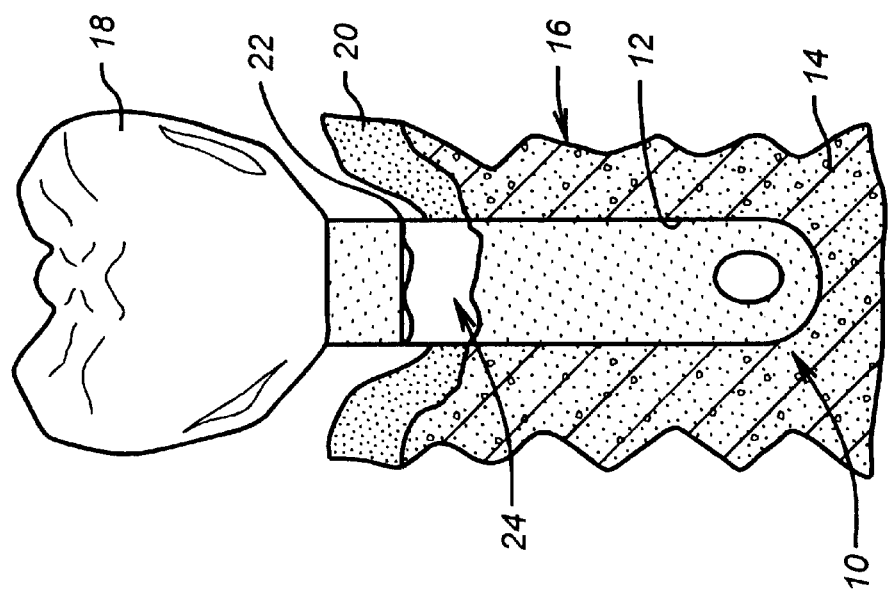
FIG. 2 is a front view similar to FIG. 1 showing an infected area about the dental implant proximate an area of saucerization.

As illustrated in FIG. 2, continued inadequate stimulation of the bone tissue leads to further resorption of bone tissue. Ultimately, the depletion of bone tissue can create a pocket in the gingival tissue which exposes the textured implant surface, making it susceptible to infectious agents from the oral cavity. Additionally, the dental implant may become destabilized and loose within cylindrical bore 12. In any of these situations, failure of the dental implant may result.

Figure 3:
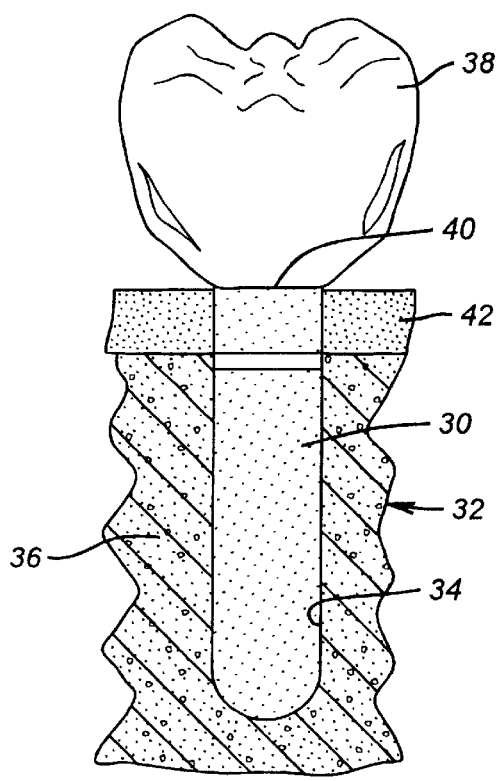
FIG. 3 is a front view similar to FIG. 1 but showing the lack of saucerization when the dental implant is constructed according to the present invention.

However, if sufficient stimulation is provided to the bone tissue, the stress shielding phenomenon can be avoided, as illustrated in conjunction with an exemplary embodiment of the present invention shown in FIG. 3. In this illustrated embodiment, a preferred dental implant 30 is designed to dissipate forces throughout surrounding tissue. The dental implant 30 is disposed at an implant site 32 within a cylindrical bore 34 formed in an area of bone tissue 36.

A prosthetic tooth 38 and an appropriate abutment 40 are shown mounted to dental implant 30. As described above, a layer of gingival tissue 42 typically is disposed between bone tissue 36 and prosthetic tooth 38. The unique design of dental implant 30 provides a reduced stiffness or flexibility of the implant that results in sufficient bone tissue stimulation to avoid the detrimental effects of stress shielding. As illustrated, the bone tissue 36 remains healthy and in place along the complete length of dental implant 30 beneath gingival tissue 42.

Figure 4:
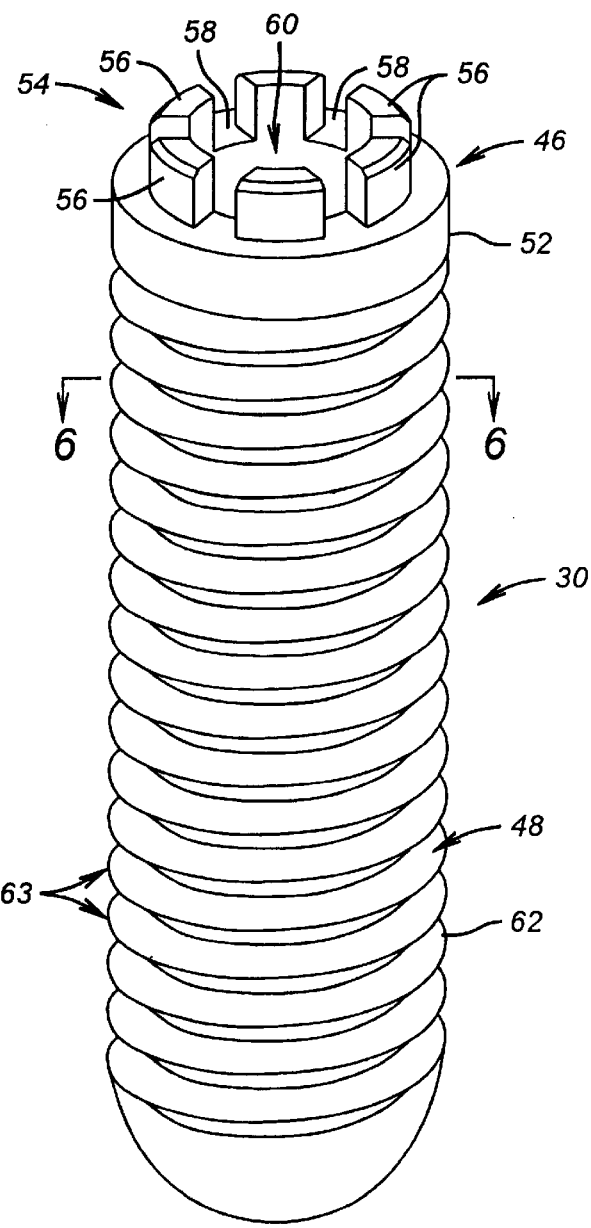
FIG. 4 is a perspective view of a dental implant according to an exemplary embodiment of the present invention.

Referring also to FIGS. 4 and 5, dental implant 30 comprises an implant body having a core 44, a mounting end 46 and a shell 48. Preferably, core 44 and mounting end 46 are integrally connected, and they typically are formed as a single unitary structure. Both core 44 and mounting end 46 are formed, for example, from a metallic material, such as titanium or a titanium alloy (e.g. Ti6AI4V).

In the illustrated embodiment, core 44 is generally cylindrical and defined by an outer surface 50. Outer surface 50, in turn, is circular in cross-section, as illustrated best in FIG. 6. However, although other shapes/cross-sections can be utilized. Also, core 44 is sufficiently elongated to extend into shell 48, and preferably through a majority of the length of shell 48.

Mounting end 46 typically includes an annular expanded portion 52 adjacent core 44. A mounting feature 54 is connected to annular expanded portion 52 on the side opposite core 44. Often, mounting feature 54 is structured as an anti-rotational mechanism that prevents rotation of prosthetic tooth 38. In the illustrated embodiment, mounting feature 54 includes a plurality, e.g. six, splines 56 that extend outwardly from annular expanded portion 52 in an axial direction generally opposite core 44. A gap 58 is disposed between each adjacent pair of splines 56. Additionally, mounting end 46 includes an axial, threaded bore 60 disposed at a generally central location that is radially inward from splines 56. Axial bore 60 may extend into core 44, and it facilitates the mounting of abutment 40 and prosthetic tooth 38.

In the illustrated embodiment of the invention, shell 48 is cylindrical in shape and has an outer surface 62 that is circular in cross-section, as best illustrated in FIG. 6. Shell 48 and outer surface 62 are sized for engagement with cylindrical bore 34 formed in bone tissue 36. Potentially, outer surface 62 can be smooth or textured. Additionally, outer surface may comprise a threaded region 63 (see FIG. 4), depending on the particular dental implant application.

Shell 48 also includes an axial opening 64 having a length and cross-section formed to receive core 44. A wall 66 is effectively created between axial opening 64 and outer surface 62. The thickness of wall 66 is sufficient to place outer surface 62 in general axial alignment with the radially outer surface of annular expanded portion 52.

Shell 48 is made from a material that is less stiff than core 44. Specifically, the preferred material of shell 48 has a lower modulus of elasticity than that of core 44. Preferably, the material of shell 48 has a modulus of elasticity that is similar to the modulus of elasticity of bone tissue 36.

The material of shell 48 may be a polymeric material, such as polyetheretherketone, commonly known as PEEK. PEEK has the characteristics of high strength, low water absorption and biocompatibility, as well as having a modulus of elasticity much closer to that of the surrounding bone than the typical titanium or titanium alloy core 44. To increase the strength of a polymer, such as PEEK, the polymer may be reinforced with a fiber or fibers, such as a carbon fiber, to create a polymeric composite. Thus, the polymeric material retains the desired flexibility and resiliency that permits transfer of mastication forces to bone tissue 36 throughout the entire implant site 32, while the fibers provide strength and thermal stability.

A primary example of such a composite material is carbon fiber reinforced (CFR) PEEK. CFR PEEK material may be formed by way of a filament winding process or a braiding process. Furthermore, the shell 48 may be formed by creating opening 64 in a solid rod or cylinder of PEEK reinforced with either chopped or continuous carbon fibers depending on the desired material characteristics. Accordingly, the desired strength of shell 48 potentially can be adjusted by selection of both the length and orientation of the carbon fibers throughout the PEEK material. For example, to withstand the mastication loads exerted on dental implant 30 during chewing, it may be desirable to use continuous fiber reinforcement of the PEEK material.

Core 44 and shell 48 may be attached to one another by a variety of methods. For example, the two components may be attached by resistive heating of the titanium alloy (e.g. TiA14V) core or by induction heating of core 44. Other potential methods of attachment include microwave radiation to partially melt the PEEK material, or attachment by spin welding, a method by which the two components are assembled while one or the other is spinning. If the spin rate is sufficiently high, frictional forces at the interface between core 44 and shell 48 cause the PEEK to melt. As the speed of spinning is then reduced, the PEEK material of shell 48 adheres to the metallic material of core 44 and forms a bond. Other methods of attachment include high temperature compression molding, ultrasonic welding and conventional, biocompatible adhesives.

The lower modulus material utilized in forming shell 48 should have sufficient flexibility to permit the transfer of forces from prosthetic tooth 38 to bone tissue 36. Effectively, outer surface 62 of shell 48 bends and moves a sufficient amount to permit the transfer of forces to bone tissue 36. The transfer of forces reduces or eliminates the saucerization/resorption of bone tissue beneath gingival layer 42 that can otherwise occur.

In a slightly modified embodiment illustrated in FIG. 7, surface 62 of shell 48 has been covered with an outer layer 68 designed to further promote osseointegration. Outer layer 68 may comprise a thin layer of titanium laid over a PEEK composite shell or substrate. The titanium layer may be placed on the PEEK material by, for example, a technique known as vapor deposition.

Outer layer 68 also may comprise other materials. For example, hydroxylapatite (HA) may be deposited as layer 68 through an electrochemical deposition technique. Alternatively, outer layer 68 may be a coating of biologically active molecules such as proteins, growth factors or synthetic peptides or other materials that improve the in vivo attachment of bone tissue to the dental implant.

It will be understood that the foregoing description is of preferred embodiments of this invention, and that the invention is not limited to the specific forms shown. For example, a variety of mounting end configurations may be utilized; a variety of core materials can provide sufficient strength and stiffness; and other materials potentially may be used in the construction of the shell. These and other modifications may be made in the design and arrangement of the elements without departing from the scope of the invention as expressed in the appended claims.

What is claimed is:

1. A dental implant formed from two different materials, comprising:
   an implant body including, a metallic core forming the first material, and an anti-rotational mounting feature at a proximal end of the metallic core; and
   a shell disposed about the metallic core, the shell forming the second material, having an inner surface directly contacting the core, having an outer surface for contacting bone, and having a lower modulus of elasticity than the metallic core, wherein the shell comprises a PEEK material.

2. The dental implant as recited in claim 1, wherein the PEEK material is a carbon fiber reinforced PEEK material.

3. The dental implant as recited in claim 2, wherein the metallic core comprises a titanium alloy.

4. The dental implant as recited in claim 3 wherein the carbon fiber reinforced PEEK material comprises a continuous fiber PEEK material.

5. The dental implant as recited in claim 1, wherein the metallic core has a body portion with an elongated cylindrical shape, the inner surface of the shell contacts substantially all of the body portion, and the inner surface of the shell is directly bonded to the metallic core.

6. The dental implant as recited in claim 1, wherein the shell is bonded to the metallic core by a spin weld.

7. The dental implant as recited in claim 1, wherein the shell is bonded to the metallic core by an adhesive.

8. The dental implant as recited in claim 1, wherein the shell is bonded to the metallic core by ultrasonic welding.

9. A dental implant formed from two materials and designed for implantation at an implant site in a jawbone of a patient, the implant site including a cylindrical hole formed in the jawbone, the dental implant comprising:
   a metallic core; and
   a shell including inner and outer surfaces, the inner surface formed from a recessed opening sized to receive and directly contact the metallic core, the outer surface sized to fit within the cylindrical hole and engage the jawbone, wherein the shell is a softer material than the metallic core, wherein the shell comprises a PEEK material.

10. The dental implant as recited in claim 9, wherein the shell comprises a plastic material having a modulus of elasticity lower than that of the metallic core.

11. The dental implant as recited in claim 9, wherein the PEEK material comprises a carbon fiber reinforced PEEK material.

12. The dental implant as recited in claim 9, further comprising a coating applied to the outer surface.

13. The dental implant as recited in claim 12, wherein the coating comprises a titanium material.

14. The dental implant as recited in claim 12, wherein the coating comprises a hydroxylapatite material.

15. The dental implant as recited in claim 12, wherein the coating comprises a biologically active molecule material.

16. A dental implant for implantation into a jawbone, comprising:
   a metallic core having an elongated body portion; and
   a shell formed from a material, having an inner surface surrounding and contacting the body portion of the core, and having an outer surface adapted to interface with the jawbone.

17. The dental implant as recited in claim 16, wherein the inner surface of the shell is directly bonded to the core, and wherein the shell is adapted to distribute a substantial portion of forces generated during mastication to the jawbone surrounding the shell.

18. The dental implant as recited in claim 17 wherein the outer surface of the shell is threaded.

19. The dental implant as recited in claim 16 wherein the body portion has a cylindrical configuration with an internally threaded shaft, the inner surface of the shell is permanently bonded to the body portion, the core has a proximal end adjacent the body portion, the proximal end is above the shell and adapted to engage a dental prosthesis, and the proximal end includes an annular flange abutting against the shell.

20. The dental implant as recited in claim 16 wherein the outer surface of the shell is coating with HA or biologically active molecules such as proteins, growth factors or synthetic peptides or other materials that improve the in vivo attachment of bone tissue to the dental implant.

* * * * *